United States Patent [19]

Meyer

[11] 3,970,785
[45] July 20, 1976

[54] TONE COUNT AUDIOMETRIC COMPUTER

[75] Inventor: Charles R. Meyer, San Antonio, Tex.

[73] Assignee: The United States of America as represented by the Secretary of the Air Force, Washington, D.C.

[22] Filed: May 13, 1975

[21] Appl. No.: 577,133

[52] U.S. Cl. ................................ 179/1 N
[51] Int. Cl.² .............................. H04R 29/00
[58] Field of Search ....................... 179/1 N

[56] References Cited
UNITED STATES PATENTS

| | | | |
|---|---|---|---|
| 3,536,835 | 10/1970 | Ramer | 179/1 N |
| 3,793,485 | 2/1974 | Feezer | 179/1 N |

Primary Examiner—Kathleen H. Claffy
Assistant Examiner—E. Matt Kemeny
Attorney, Agent, or Firm—Joseph E. Rusz; William Stephanishen

[57] ABSTRACT

A hearing threshold level measuring apparatus for automatically determining testing hearing level in each ear and processing the test scores for either manual or automatic readout. A predetermined number of tone bursts varied randomly from one to four in each test sequence and automatically decreased in level. The subject is provided with a response panel containing pushbuttons labelled one through four. The subject's bearing threshold is then determined from his pushbutton responses to his correct burst tone counts.

9 Claims, 3 Drawing Figures

FIG.1

TONE COUNT AUDIOMETRIC COMPUTER

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to hearing level testing devices and in particular to a tone count audiometric computer apparatus for automatically determining hearing threshold levels.

In the prior art, audiometers are well known and for many years have been utilized for testing in industry, schools, the military, and others, to provide initial screening of individual hearing sensitivity, as well as by the medical profession to detect the presence of hearing defects and diseases in humans.

The prior art audiometers generally comprise a tone generator portion for furnishing audio signals of discrete frequencies to a set of earphones worn by the subject being tested, an intensity varying or attenuator portion for varying the intensity level of the generated tone, and some type of means for recording the hearing sensitivity of the individual being tested in response to the varying frequency and intensity tones being presented thereto.

The increased reliance upon the audiometer has dictated that the testing apparatus be substantially automatic or self-recording to reduce dependency upon operator-technician accuracy and provide a permanent and accurate record of the hearing status of both ears of the subject being tested. In addition, it has been found that some means be incorporated into the audiometer which can detect the malinger or one who is intentionally attempting to alter the true test results.

SUMMARY OF THE INVENTION

The present invention determines hearing level by presenting a predetermined number of tone bursts at a given hearing level and recording the number of correct responses with respect thereto. The number of tone bursts varies randomly from one through four in each test sequence. Four numbered response buttons are provided to record the number of tone bursts which were heard at a given hearing level. The first sequence of tone bursts for each frequency occurs at 30 DB HL. The test proceeds until two sequential ascents through threshold in increments of 5 DB result in similar threshold determinations within a 5 DB tolerance. The subject's hearing threshold level is then defined at the lower of two threshold determinations. Multiple inconsistent mistakes are allowed without affecting a subject's final score, since two sequentially consistent ascents are required before scoring occurs.

It is one object of the invention, therefore, to provide an improved audiometric computer apparatus wherein a predetermined number of tone bursts at a given hearing level are provided.

It is another object of the invention to provide an improved audiometric computer apparatus having a variable number of tone burst in each test sequence.

It is still another object of the invention to provide an improved audiometric computer apparatus wherein the number of tone burst in a test sequence are randomly varied.

It is yet another object of the invention to provide an improved audiometric computer apparatus having a test sequence which has sequential ascents through threshold in 5 db increments to establish threshold determinations.

These and other advantages, features and objects of the invention will become more apparent from the following description taken in connection with the illustrative embodiment in the accompanying drawings.

DESCRIPTION OF THE PREFERRED EMBODIMENT

Figure 1:
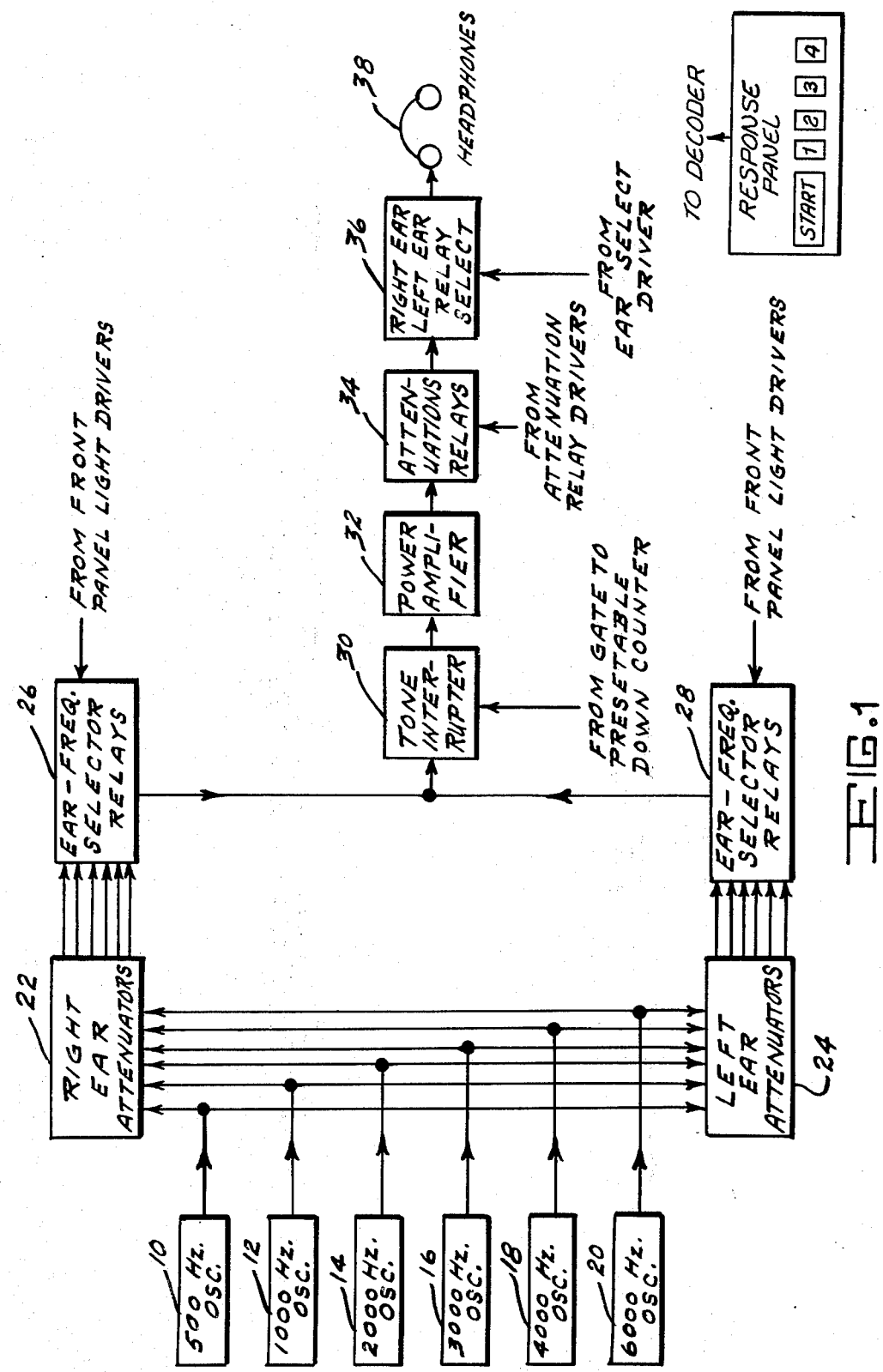
FIG. 1 is a block diagram of the audiometric hearing test apparatus in accordance with the present invention.

Referring now to FIG. 1, there is shown a tone count audiometric computer apparatus having a plurality of oscillators 10–20 to generate the various frequency signals which will be utilized to determine hearing level threshold. The outputs from the plurality of oscillators 10–20 are applied simultaneously to attenuators 22, 24 and then respectively to ear-frequency selector relays 26, 28. The ear-frequency relay selectors 26, 28 are connected to a tone interrupter unit 30 which applies selected frequencies in bursts to the power amplifier 32. The power amplifier 32 is connected through the attenuation relays 34 to the right/left ear selector unit 36 which is connected to the earphones 38. Input signals from the computing unit (not shown) control the start of the testing sequence, the intensity of the test frequency and the selection of the ear to be tested.

The tone count and diametric computer apparatus implements the Hughson-Westlake protocol which is normally used in clinical pure-tone audiometry for determining hearing threshold levels. The protocol begins the test for each frequency at a presentation level or intensity that the subject is likely to hear, such as 30 dB, to acquaint the subject with the tone used. The level of presentation is then decreased in steps of 10 dB until the examinee fails to indicate his hearing of the tone. At this point the level is increased in 5 dB steps and the intensity at which the examinee first hears the tone is noted. The intensity is then decreased in 10 dB steps until the tone is no longer heard. The ascent in 5 dB steps is then repeated. This procedure of increasing in 5 dB steps until the examinee hears the tone and then decreasing in 10 dB steps until he no longers hears the tone is repeated until agreement within 5 dB occurs between two levels at which he first hears the tone during three consecutive ascents. This common or lower value is stored in memory as the examinee's hearing threshold level for that frequency and ear.

The method of determining the examinee's detection of tones utilizes tone counting. The examinee is presented a number of tone bursts at a given intensity and must hear them sufficiently well enough to count them. The number of tone bursts in each tone train is varied pseudorandomly in the range from 1 through 4 tones. The examinee indicates the number of tones heard by depressing the appropriately numbered button on a response panel which is appropriately numbered.

Figure 2:
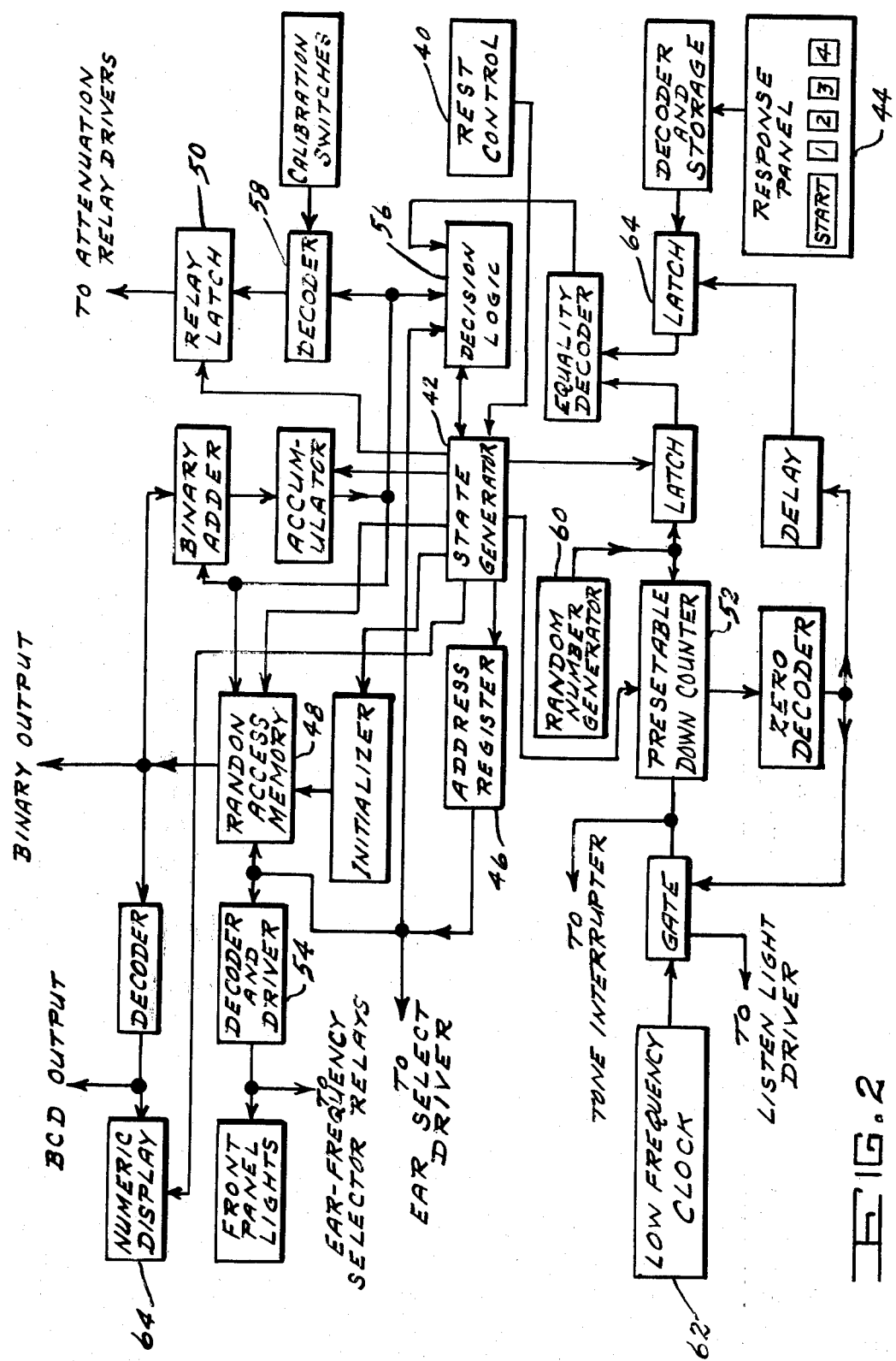
FIG. 2 is a block diagram of the computing subunit of the audiometric hearing test apparatus.
Figure 3:
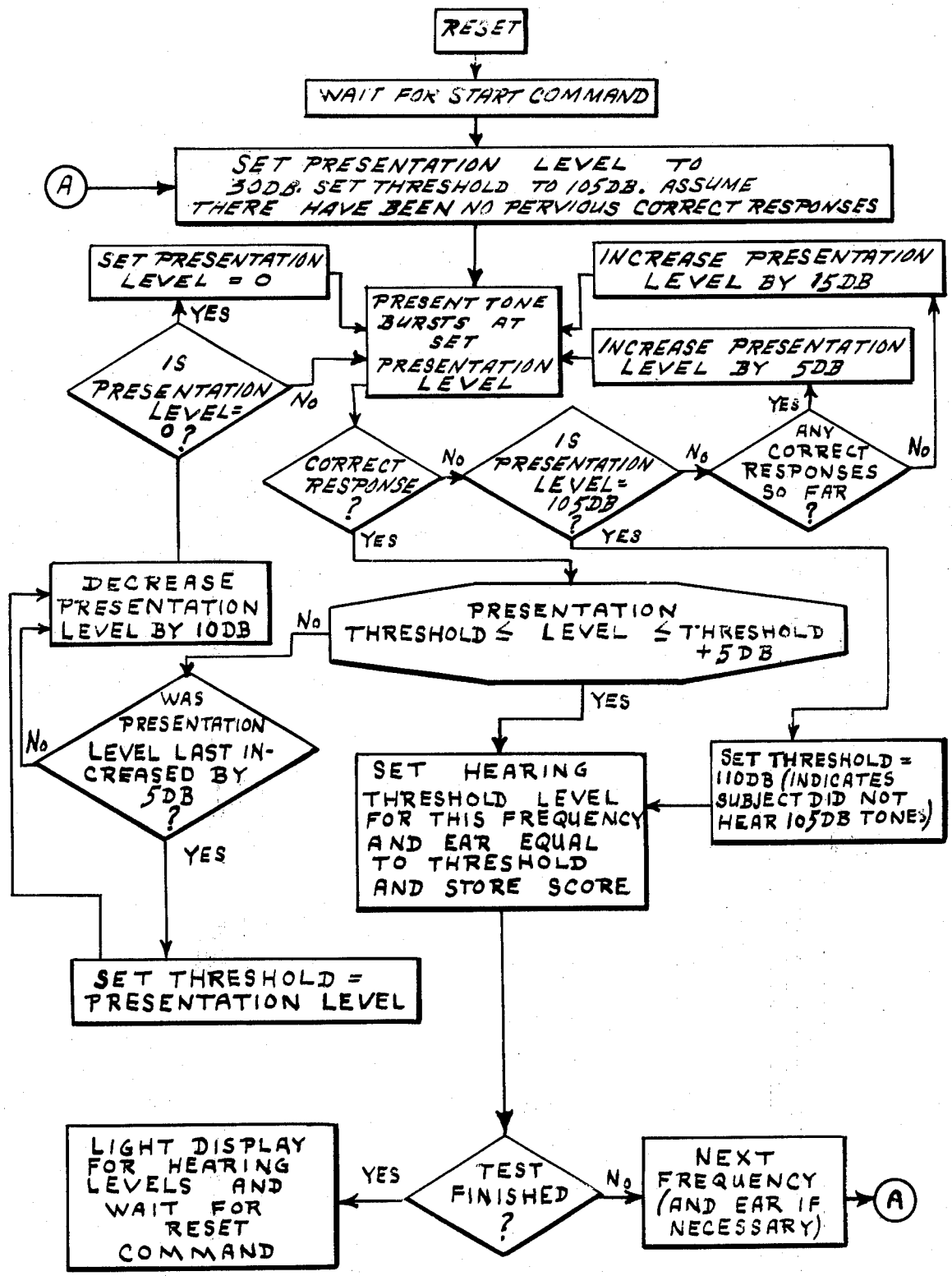
FIG. 3 is a flow diagram of the hearing test decision sequence for the audiometric hearing test apparatus.

Turning now to FIG. 2, there is shown the computing means of the audiometric computer apparatus having a reset control unit 40 connected to the state generator 42. The reset control 40 is activated to place the computing means in an idle state (state 1) until the examinee presses the start button which is shown on the response panel 44. The program counter or state generator 42 then enters several states that initialize the contents of the address register 46, the random access memory 48, the latch relay 50, and the presetable down counter 52 which correspond to the variables of ear and frequency and current tone presentation level. The signals to the ear-frequency selector and the ear selector of FIG. 1 are four bit binary words. The most significant bit corresponds to the ear being tested or reviewed (E=0 for right ear; E=1 for left ear.) The three remaining bits correspond to one of 6 frequencies being generated or reviewed (F=000 through 101). The decimal value of the binary contents of counter 52 correspond to one-fifth the hearing presentation level or intensity, G, of the tones in dB units. Thus, G=00110 corresponds to a presentation level of 30 dB. The constants K2 and K3 are frequently used values and are stored in random access memory 48. The register 46 is used to remember whether any previous correct answers have occurred in the test sequence for the existing ear and frequency combination. Register 46 is initialized to logical 0 and later set to logical 1 at the occurrence of the first correct answer. In each test on a given ear and frequency is started at 30 dB, a level most examinees can hear. However, if he cannot hear the tones or is uncertain of his role in the test, the intensity is increased in 15 dB steps until he either gives a correct response or the tone count audiometric computer apparatus reaches the top of its intensity range. After the first correct response, the normal Hughson-Westlake protocol is entered and all succeeding intensity increments occur in 5 dB steps. The register J in the decoder and driver unit 54 is initialized to a logical 0 and set to a logical 1 when in the 5 dB ascent phase of the Hughson-Westlake protocol. The contents of the register thresh, T, which is located in decision unit 56 are initialized at the top of the tone count audiometric computer apparatus's intensity range and are modified to equal the contents of decoder 58 at each correct answer following the 5 dB ascent phase. The contents of register T are used to check agreement within 5 dB of presentation levels at which the examinee first hears the tones during two consecutive ascents. When agreement occurs, register T contains the value defined as the examinee's hearing threshold level for that ear and frequency. The state generator 42 then enters State 10 in which the analog switch (tone interrupter) is prepared for future action and the latch whose contents control the relay-selected tone attenuation sections is loaded with the contents of decoder 58. The loading of the latch causes the relays to set. The next program counter state of state generator 42 causes a number from the high frequency counter or random number generator 60 (count sequence 1, 2, 3, 4, 1 . . .) to be selected. This number selection presets the down counter 52 such that it will be toggled down to the zero state by a slow clock 62. Before the count down is started a cycle of the same slow clock 62 is used to flash a light on the examinee's panel response unit 44 warning him to listen carefully for the subsequent presentation of tones. Each state of the down counter 52 is used to allow a tone to pass through the analog tone interrupter circuit to the earphones. Thus, a tone train is presented to the examinee's earphones. The fall and rise times of each tone in the train are 25 milliseconds and each tone's duration is 330 milliseconds. Each silent period separating tones within a tone train is also 330 milliseconds (50 percent duty factor). While the down counter 52 is slowly being toggled towards zero and for a short period afterward, the state generator 42 waits in State 11. After the last tone in the train occurs a monostable generator in the panel response unit 44 is used to cause a time delay (typically 1.8 to 2.0 seconds) during which the examinee may respond by depressing the appropriately numbered button. At the end of the time delay, the examinee's last response is transferred to the latch unit and the state generator 42 continues. The next state checks an equality circuit to determine if the examinee's response was correct. The program from this point contains many possible sequences and is best described by the flow chart which is shown in FIG. 3. At the end of the audiometric test, the state generator 42 enters and remains in State 37 during which time the seven-segment digital display 64 is unblanked for viewing the examinee's hearing threshold levels for all ear and frequency combinations.

The results are presented singly in the same sequence as they were acquired during the test. Each result for the next ear and frequency combination is viewed by depressing an examine button once. The results may be viewed as often as desired or the tone count audiometric computer apparatus may be interrogated automatically by another digital data acquisition device (computed, data logger, etc.).

The tone count audiometric computer apparatus is made ready for the next test by depressing a reset button or by providing an external, TTL compatible signal. As this point, the state generator 42 enters State 1 and the data from the previous examination is no longer available. The state generator 42 proceeds again only when the next examinee presses his start button.

Although the invention has been described with reference to a particular embodiment, it will be understood to those skilled in the art that the invention is capable of a variety of alternative embodiments within the spirit and scope of the appended claims.

What is claimed is:

1. A tone count audiometric computer apparatus comprising in combination:
    a tone generating means for providing a plurality of different frequency tones, said tone generating means being controllable in frequency tone level, said tone generating means being programable as to the ear to be tested,
    a logical control means connected to said tone generating means for controlling said frequency tone level, said logical control means selecting the frequency tones to be applied to the ear under test, said logical control unit providing an ear-select signal to said tone generating means to test a particular ear, said logical control means providing a tone interrupt signal to said tone generating means to provide a plurality of different tone burst to said ear under test, and
    a response panel unit connected to said logical control means to record the number of different tone bursts heard, said response panel unit having a start testing sequence control signal, said response panel unit having a testing ready indication and a listen indication.

2. A tone count audiometric computer apparatus as described in claim 1 wherein said tone generating means comprises in combination:
- a plurality of frequency generating means to provide a plurality of different frequency tones,
- a first and second attenuation means connected respectively to said plurality of frequency generating means, said first attenuation means controlling said frequency tone to a first ear, said second attenuation means controlling said frequency tone to a second ear, said first and second attenuation means being mutually exclusively,
- a first and second ear-frequency selector means to respectively select frequency tones for the ear under test, said first and second ear-frequency selector means being respectively connected to said first and second attenuator means, said first and second ear-frequency selector means respectively receiving frequency-select signals from said logical control means,
- a tone burst control means connected to said first and second ear-frequency selector means respectively to receive said plurality of different frequency tones, said tone burst control means receiving said tone interrupt signal from said logical control means to provide a plurality of random tone bursts, said tone burst control means receiving a level control signal from said logical control means to control the amplitude of said plurality of random tone bursts, and
- an ear select unit connected to said tone burst control means to select the ear under test, said ear select unit receiving an ear-select signal from said logical control means.

3. A tone count audiometric computer apparatus as described in claim 1 wherein said tone burst control means comprises in combination:
- a tone interrupter unit to provide tone bursts, said tone interrupter unit receiving said plurality of different frequency tones, said tone interrupter unit receiving said tone interrupt signal from said logical control means,
- a power amplifier unit connected to said tone interrupter unit to receive and amplify said tone bursts, and,
- an attenuation unit connected to said power amplifier unit to receive said amplified tone bursts, said attenuation unit receiving a level control signal from said logical control means, said attenuation unit adjusting the amplitude of said amplified tone bursts in response to said level control signal.

4. A tone count audiometric computer apparatus as described in claim 1 wherein said plurality of different tone bursts equals four.

5. A tone count audiometric computer apparatus as described in claim 1 wherein said plurality of different tone bursts are more than one.

6. A tone count audiometric computer apparatus as described in claim 1 wherein said response panel unit is manually activated by the subject to provide a plurality of burst response signals to said logical control means.

7. A tone count audiometric computer apparatus as described in claim 1 wherein said plurality of random tone bursts are greater than one.

8. A tone count audiometric computer apparatus as described in claim 1 wherein said plurality of random tone bursts equals four.

9. A tone count audiometric computer apparatus as described in claim 6 wherein said plurality of burst response signals equals four.

* * * * *